(12) United States Patent
Paulus (10) Patent No.: US 10,564,113 B2
(45) Date of Patent: Feb. 18, 2020

(54) MATERIAL IDENTIFICATION METHOD

(71) Applicant: COMMISSARIAT A L'ENERGIE ATOMIQUE ET AUX ENERGIES ALTERNATIVES, Paris (FR)

(72) Inventor: Caroline Paulus, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 205 days.

(21) Appl. No.: 15/742,191

(22) PCT Filed: Jul. 7, 2016

(86) PCT No.: PCT/FR2016/051720
§ 371 (c)(1),
(2) Date: Jan. 5, 2018

(87) PCT Pub. No.: WO2017/006059
PCT Pub. Date: Jan. 12, 2017

(65) Prior Publication Data
US 2018/0195981 A1 Jul. 12, 2018

(30) Foreign Application Priority Data
Jul. 8, 2015 (FR) ...................................... 15 56461

(51) Int. Cl.
*G01N 23/087* (2018.01)

(52) U.S. Cl.
CPC ....... *G01N 23/087* (2013.01); *G01N 2223/04* (2013.01); *G01N 2223/206* (2013.01); *G01N 2223/345* (2013.01); *G01N 2223/426* (2013.01)

(58) Field of Classification Search
CPC ...... G01N 23/00; G01N 23/087; G01N 23/06; G01N 23/083; G01N 2223/345;
(Continued)

(56) References Cited

U.S. PATENT DOCUMENTS

| 5,768,334 A | 6/1998 | Maitrejean et al. |
| 6,118,850 A | 9/2000 | Mayo et al. |

(Continued)

FOREIGN PATENT DOCUMENTS

WO 94/28442 A1 12/1994

OTHER PUBLICATIONS

International Search Report dated Nov. 2, 2016, in PCT/FR2016/051720 filed Jul. 7, 2016.
(Continued)

*Primary Examiner* — Jurie Yun
(74) *Attorney, Agent, or Firm* — Oblon, McClelland, Maier & Neustadt, L.L.P.

(57) ABSTRACT

A method for identifying a material contained in a sample. The sample is subjected to irradiation via ionizing electromagnetic radiation, for example X-rays. The sample is inserted between a source emitting the radiation and a spectrometric detector configured to acquire a spectrum of the radiation transmitted by the sample. The spectrum is subject to different treatment operations to enable classification of the material. The steps are, consecutively: reducing dimensionality, followed by projecting along the predefined projection vectors. Projection makes it possible to establish classification parameters, on the basis of which classification is established.

13 Claims, 6 Drawing Sheets

(58) Field of Classification Search
CPC ....... G01N 2223/426; G01N 2223/206; G01N 2223/04; G01N 2223/303; G01D 18/00
USPC .................................. 378/53, 56, 207, 901
See application file for complete search history.

(56) References Cited

U.S. PATENT DOCUMENTS

| | | |
|---|---|---|
| 6,266,390 B1 | 7/2001 | Sommer, Jr. et al. |
| 2001/0022830 A1 | 9/2001 | Sommer, Jr. et al. |
| 2003/0147494 A1 | 8/2003 | Sommer, Jr. et al. |
| 2005/0078786 A1 | 4/2005 | Sommer, Jr. et al. |
| 2006/0013360 A1 | 1/2006 | Sommer, Jr. et al. |
| 2006/0239401 A1 | 10/2006 | Sommer, Jr. et al. |
| 2008/0279329 A1 | 11/2008 | Sommer, Jr. et al. |
| 2010/0111252 A1 | 5/2010 | Sommer, Jr. et al. |
| 2011/0222654 A1 | 9/2011 | Sommer et al. |

OTHER PUBLICATIONS

Article 94(3) Communication issued in corresponding European Application No. 16 747 830.4 dated Oct. 16, 2019, citing below AX-AY references.

Wang et al., "Material separation in x-ray CT with energy resolved photon-counting detectors," Medical Physics, AIP, Melville, NY, vol. 38, No. 3, Feb. 24, 2011, pp. 1534-1546.

Alessio et al., "Quantitative material characterization from multi-energy photon count CT," Medical Physics, AIP, Melville, NY, vol. 40, No. 3, Feb. 28, 2013, pp. 31108-31108.

Fig. 8 ized electromagnetic radiation, followed by a spectrometric analysis of the radiation transmitted by the irradiated material. More precisely, the invention is a method of analysis implementing a combining of measured spectrometric data, followed by a projection of the combined data with the aid of previously determined projection vectors.

MATERIAL IDENTIFICATION METHOD

TECHNICAL FIELD

The technical field of the invention is the identification of a material by irradiation with the aid of an ionizing electromagnetic radiation, followed by a spectrometric analysis of the radiation transmitted by the irradiated material. More precisely, the invention is a method of analysis implementing a combining of measured spectrometric data, followed by a projection of the combined data with the aid of previously determined projection vectors.

PRIOR ART

The determination of the nature of materials by irradiation with the aid of X-rays is a standard technique, practiced for decades. There are an uncountable number of industrial systems based on the irradiation of an object by X-ray radiation, and analysis of the radiation transmitted by the object, the latter being interposed between an X-ray source and a detector. Such systems are used daily, for example in the checking of airport baggage.

Initially intended to discriminate dense materials, for example metals, these technologies have advanced and have made it possible to identify lightweight materials, liable to present a risk. A notable advance has been the implementation of spectrometric detectors, allowing the acquisition of utilizable spectra, while being exposed to significant fluxes.

For example, patent EP2510338 describes a method making it possible to determine the nature of a material, and of its thickness, on the basis of a spectrum of X-ray radiation transmitted by said material. Coefficients ($\alpha_1 \ldots \alpha_n$), termed attenuation or transmission coefficients, are calculated on the basis of the spectrum. A calibration database is also available, produced with various calibration samples, the nature and the thickness of each calibration sample being known. For a material of the same nature, several calibration samples of different thicknesses are available. Thus, each calibration sample corresponds to a pair (nature of the material; thickness), with which are associated coefficients ($\alpha_1^{u,v}, \ldots \alpha_n^{u,v}$) the exponents u and v designating respectively the nature of the material constituting the calibration sample as well as its thickness.

The calibration sample (material u–thickness v) whose attenuation coefficients ($\alpha_1^{u,v} \ldots \alpha_n^{u,v}$) are closest to the measured coefficients ($\alpha_1 \ldots a_n$) is identified in the database with the help of the coefficients ($\alpha_1 \ldots \alpha_n$) arising from a spectrum of the radiation transmitted by an unknown material. The nature of the material constituting the object, as well as its thickness, are then considered to be those corresponding to the calibration sample exhibiting the coefficients closest to the object.

More recently, document WO2015091083 describes a method making it possible to estimate the effective atomic number $Z_{eff}$ of a material. Effective atomic number is understood to mean a combination of the atomic numbers of the chemical elements constituting the material. The combination takes the form in particular of a weighted sum, by assigning the atomic number of each chemical element a weighting coefficient dependent on the mass fraction or atomic fraction of said chemical element in the material. Thus, if each chemical element constituting the material is indexed by the index k, a possible definition of $Z_{eff}$ can be:

$$Z_{eff} = \left( \sum_{k=1}^{K} \eta_k (Z_{eff}^k)^z \right)^{1/z}$$

with:
- $\eta_k$: mass fraction of chemical element k in the material;
- K: number of chemical elements in the material;
- z: constant equal to 4.62.

Such an estimation can be established by applying a likelihood function to the spectrum of the X-ray radiation transmitted by the analyzed material. The likelihood function is established previously, with the aid of calibration measurements, implementing calibration materials, whose atomic number and thickness are known. The effective atomic number of the analyzed material can in particular be obtained by implementing an algorithm of maximum likelihood type, the effective atomic number and the thickness being those which maximize the likelihood function.

The inventors have sought to enhance the above-described schemes, by proposing a more precise evaluation of the nature of the material, making it possible to establish an estimation of the nature of the material, independently of its thickness.

DISCLOSURE OF THE INVENTION

A subject of the invention is a method for classifying a material comprising the following steps:
i) irradiation of a sample, comprising said material, with the aid of an electromagnetic ionizing radiation, termed the incident radiation, produced by an irradiation source;
ii) detection of a radiation transmitted by said sample with the aid of a spectrometric detector, said sample being disposed between said irradiation source and said detector, and acquisition of a spectrum of the radiation thus detected, termed the transmission spectrum, representative of the energy distribution of said radiation transmitted, the spectrum comprising a number of channels and representing a quantity of photons detected per channel, each channel corresponding to an energy range;
iii) determination of a set of parameters with the help of the transmission spectrum, this set of parameters forming the coordinates of a vector of parameters, representing said transmission spectrum, in an input space;
iv) projection of said vector of parameters according to at least one projection vector, so as to obtain at least one projected datum, each projected datum resulting from the projection of said vector of parameters according to a projection vector;
v) classification of the material as a function of each projected datum.

According to one embodiment, there is a plurality of projection vectors, step iv) making it possible to obtain a plurality of projected data, each projected datum resulting from the projection of the parameter vector according to a projection vector.

There may in particular be a predetermined number of classes of materials, step v) consisting in classifying the material according to one of said classes of material. A class of materials can correspond to a particular material or to a group of materials.

Step iv) can comprise the projection of said vector of parameters into an output space, each projection vector then forming a basis, termed the output basis, of said output space. The number of vectors forming said output basis may in particular be strictly less than the number of classes of materials.

According to one embodiment, the transmission spectrum is normalized, term by term, by a spectrum of the incident radiation, the latter being representative of the energy distribution of said incident radiation.

Preferably, the transmission spectrum comprises N channels, the number P of parameters of the set of parameters being strictly less than N, and preferably less than N/2 or indeed than N/4. Typically, the number P of parameters is less than 50, or indeed less than 30, or indeed less than 20. P may for example lie between 2 and 20.

According to one embodiment, the transmission spectrum is defined on a plurality of channels, and at least one parameter corresponds:
 a reference of the channel of the transmission spectrum comprising the maximum number of detected photons;
 or a ratio between the contents of two different channels;
 or a rate of change between the contents of two different channels;

Each projection vector can be determined in the course of a training phase, carried out with the aid of calibration materials whose nature is known, said calibration materials defining at least two distinct classes of materials, said training phase comprising:
 the obtaining of calibration spectra, each calibration spectrum being representative of the energy distribution of a radiation transmitted by a calibration material when said calibration material is disposed between said irradiation source and said spectrometric detector;
 the determination of a set of calibration parameters with the help of each calibration spectrum, this set of parameters forming the coordinates of a calibration vector, so as to obtain a plurality of calibration vectors corresponding to each class.

In this case, at least at least one projection vector is determined by calculating, and in particular by maximizing, with the help of each calibration vector, a discriminating criterion, determined by a comparison between:
 a first term representative of an inter-class dispersion of the calibration vectors;
 a second term, representative of an intra-class dispersion of the calibration vectors.

At least one projection vector can be obtained by determining, with the help of each calibration vector,
 a first matrix representative of an inter-class dispersion of the calibration vectors,
 a second matrix, representative of an intra-class dispersion of the calibration vectors,
 a third matrix, formed by a matrix product of a matrix inverse to said second matrix by said first matrix.

Preferably, each projection vector is determined by linear discrimination analysis, performed by considering each calibration vector. A projection vector can be an eigenvector of said third matrix. The linear discrimination analysis makes it possible to obtain optimal discrimination of the projected data, according to the various classes considered.

Another subject of the invention is a device for characterizing the material contained in a sample comprising:
 an irradiation source, able to emit an ionizing electromagnetic radiation, termed incident radiation, toward said sample,
 a spectrometric detector, able to detect a radiation transmitted by the sample when the sample, exposed to said incident radiation, is interposed between the irradiation source and the spectrometric detector,
 the device being characterized in that it comprises a processor, able to receive data measured by the spectrometric detector and to implement the method described hereinabove and in the subsequent description, the processor being linked to a memory in which at least one projection vector is stored.

Another subject of the invention is an information recording medium, readable by computer, comprising instructions for the execution of a method described hereinabove and in the subsequent description.

DISCLOSURE OF PARTICULAR EMBODIMENTS

Figure 1:
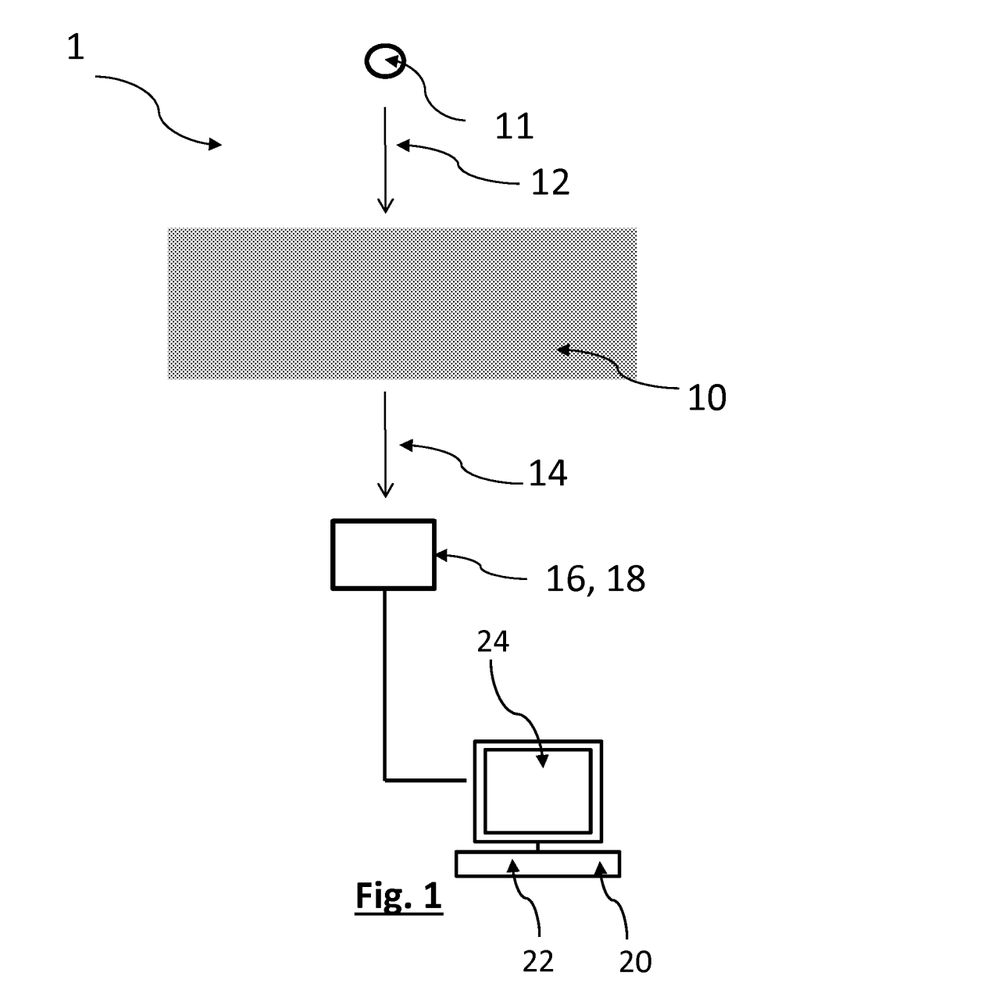
FIG. 1 represents an embodiment of a device allowing the implementation of a method according to the invention.

FIG. 1 represents an embodiment of a device 1 implementing a method according to the invention. An irradiation source 11 emits an ionizing electromagnetic radiation 12, termed the incident radiation, toward a sample 10 comprising a material to be identified. The term ionizing electromagnetic radiation designates an electromagnetic radiation of energy greater than 1 keV, and preferably less than 100 MeV. The energy range of the ionizing radiation can lie between 1 keV and 5 MeV, but it usually extends between 1 keV and 150 keV or 300 keV. The ionizing radiation can be X-ray or γ-ray radiation. Preferably, the ionizing radiation source is polyenergetic, the incident radiation being emitted according to an energy range generally extending across several tens or indeed hundreds of keV. It is in particular an X-ray emitter tube.

The thickness of the sample 10 is between a few mm and a few cm, or indeed tens of cm. It is typically less than 30 cm, or indeed 50 cm.

The sample 10 transmits a part of the incident radiation 12 to a spectrometric detector 16. Indeed, the incident radiation may undergo, in the sample, various interactions, for example a photoelectric effect, Compton inelastic scattering, or indeed a pair creation effect when the energy of the incident radiation so allows.

Hence, under the effect of the irradiation by the incident radiation 12, the sample transmits a radiation 14, termed the transmitted radiation, to a spectrometric detector 16. The spectrometric detector 16 is able to detect the transmitted radiation 14 and to form an energy spectrum of the radiation 14 thus detected.

The transmitted radiation 14 comprises a plurality of X-ray photons whose energy lies between a minimum energy $E_{min}$, and a maximum energy $E_{max}$. The detector 16 detects photons constituting this radiation and generates, when each photon is detected, an electronic pulse whose amplitude depends on the energy of the photon. More precisely, the amplitude is proportional to the energy lost by the photon in the detector, the latter energy being dependent on the energy of this photon. This detector 16 comprises an electronic spectrometry circuit 18, able to record the amplitude of each pulse generated during an acquisition period T, and to establish a histogram of the amplitude of the pulses formed during this acquisition period. An amplitude spectrum, or energy spectrum $S_p$, is then obtained, representative of the energy distribution of the radiation transmitted 14. A relation between the amplitude A and the energy E can be obtained by an energy calibration function $f$ such that $E=f(A)$, according to principles known to the person skilled in the art.

Figure 2:
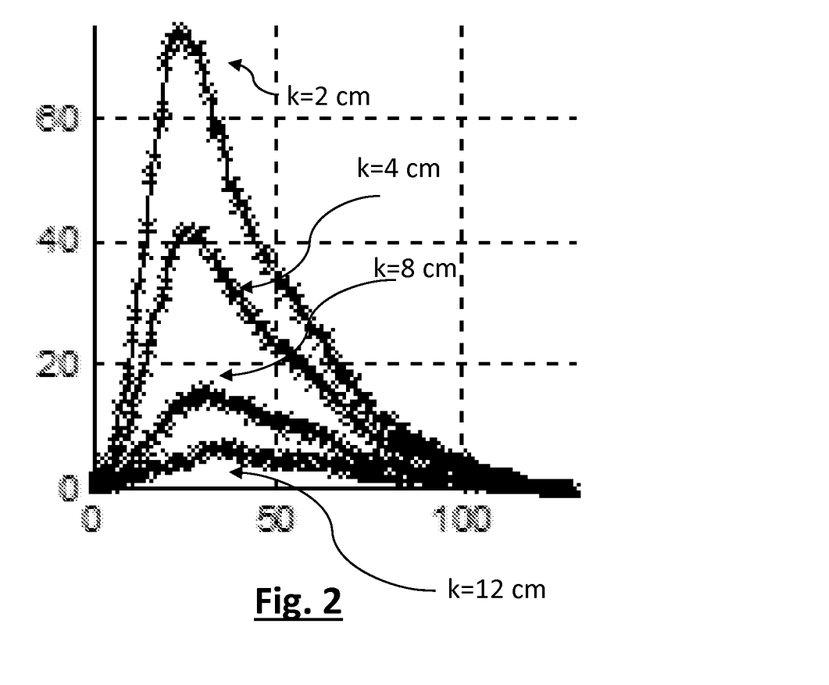
FIG. 2 represents spectra of the radiation transmitted by a polyethylene material, for various thicknesses k, respectively equal to 2 cm, 4 cm, 8 cm and 12 cm. The abscissa axis corresponds to the reference of each channel of the spectrum, while the ordinate axis represents the number of photons detected per channel.

Such a spectrum Sp is represented in FIG. 2, which represents a spectrum of the radiation 14 transmitted by polyethylene samples, whose thickness k varies between 2 cm and 12 cm. The abscissa axis corresponds to the amplitude A (or to the energy $E=f(A)$), discretized as a plurality of amplitude channels, while the ordinate axis represents the content of each channel, that is to say the number of pulses detected, or the number of pulses detected per unit time. Thus, an energy spectrum represents, for a plurality of channels, a number of photons detected per channel, each channel corresponding to an energy range. Each channel can be identified by an index n such that $1 \le n \le N$, the number of channels N being greater than or equal to 2. To each channel $E_n$ is allotted the number of pulses $Sp(E_n)$ whose energy lies in the range $E_n$ and $E_n + \Delta E_n$. For all n lying between 1 and $N-1$, $E_n \le E_{n+1}$.

The energy spectrum of the radiation 14 transmitted by the sample 10 is frequently normalized, term by term, by a spectrum $Sp_0$ established without a sample 10 interposed between the source 11 and the detector 16. The spectrum $Sp_0$ is representative of the energy distribution of the photons constituting the incident radiation 12. A spectral transmission function TR is then obtained such that, for each energy channel $E_n$, $$TR(E_n) = \frac{Sp(E_n)}{Sp_0(E_n)}$$

It is then possible to determine a spectral attenuation function Att of the sample 10, such that for each energy channel $E_n$, $Att(E_n) = -\ln[TR(E_n)]$.

In the subsequent description, a method is described whose input datum is the spectrum Sp of the radiation transmitted by the material, termed the transmission spectrum, knowing that this method applies to any spectral function implementing this spectrum, and in particular to the spectral transmission or attenuation functions such as defined above.

A processor 20, for example a microprocessor, is able to process each transmission spectrum measured by the spectrometric detector 16. In particular, the processor is a microprocessor linked to a programmable memory 22 in which is stored a sequence of instructions for performing the spectrum processing and calculation operations described in this description. These instructions can be saved on a recording medium, readable by the processor, of hard disk or CDROM type or other type of memory. The processor can be linked to a display unit 24, for example a screen.

Figure 3:
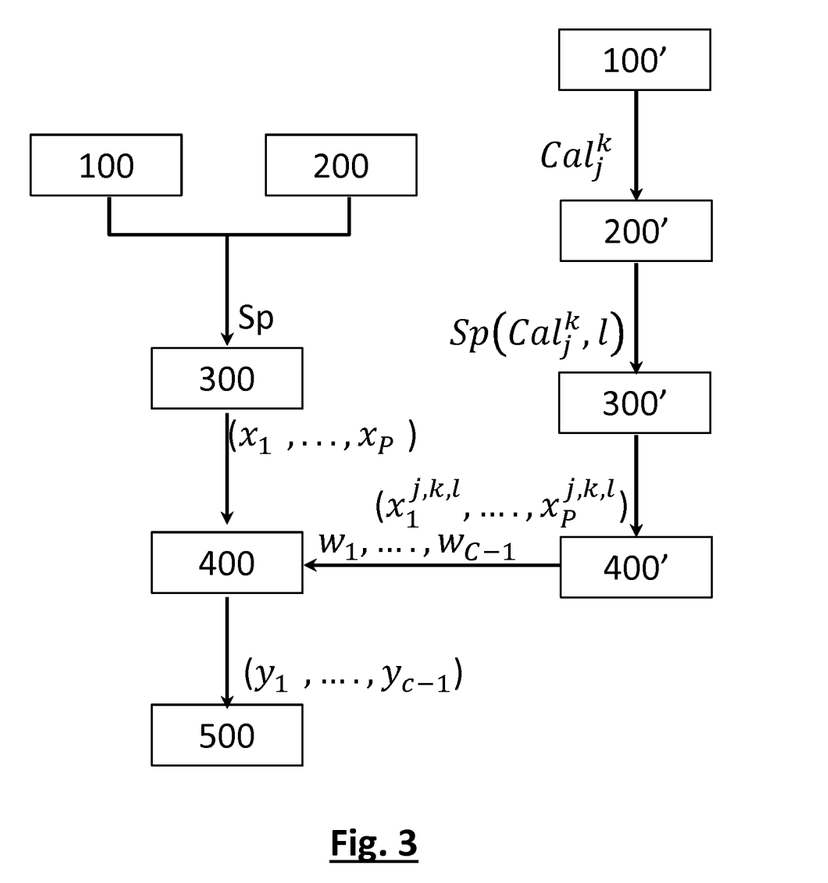
FIG. 3 represents the main steps of a method according to the invention.

The main steps of an embodiment of a method according to the invention will now be described in conjunction with FIG. 3.

The first step 100 is a step of irradiating the sample with the aid of the X-ray photon generating tube.

The second step 200 is an acquisition step, consisting in acquiring, by means of the spectrometric detector 16, a transmission spectrum Sp of a sample 10, comprising a material whose nature one wishes to determine. This step is implemented simultaneously with the first step 100. This spectrum Sp carries an item of information as regards the nature of the examined material, but this item of information is spread over the N energy channels $E_1 \ldots E_n \ldots E_N$ according to which the spectrum is defined. This number N is greater than or equal to 2, but is generally greater than 10, or indeed greater than 100. In the example considered, N=130.

The inventors have estimated that it was preferable to concentrate the item of information by reducing the number of variables, in such a way that a transmission spectrum Sp can be represented by a number P of parameters $(x_1, \ldots, x_p)$, with, preferably, $2 \le P \le 20$, and $P < N$.

Hence, in the course of a third step 300 of reducing the number of variables, or reducing the dimensionality, P parameters $(x_1, \ldots, x_p)$ representative of the transmission spectrum Sp are determined with the help of this spectrum. In this example:

the first parameter $x_1$ corresponds to the index of the channel gathering together the largest number of pulses. Thus, $x_1 = \mathrm{argmax}_n(Sp(E_n))$ the second parameter $x_2$ corresponds to a ratio between the integral of the channels extending across a spectral range $[x_1-\delta; x_1+\delta]$, of half width $\delta$, on either side of the channel referenced by the first parameter $x_1$, over the integral of the spectrum, with, in this example, $\delta=10$. Thus, $$x_2 = \frac{\sum_{n=x1-\delta}^{n=x1+\delta} Sp(En)}{\sum_{n=1}^{n=N} Sp(En)} = \frac{\sum_{n=x1-10}^{n=x1+10} Sp(En)}{\sum_{n=1}^{n=N} Sp(En)}$$

the third parameter $x_3$ corresponds to a ratio between the content of the channels located between two respective channels of index r and r+s, over the integral of the spectrum. For example, r=s=30, thus:

$$x_3 = \frac{\sum_{n=r}^{n=r+s} Sp(En)}{\sum_{n=1}^{n=N} Sp(En)} = \frac{\sum_{n=30}^{n=60} Sp(En)}{\sum_{n=1}^{n=N} Sp(En)}$$

the fourth parameter $x_4$ corresponds to a ratio between the content of channels in a low-energy range, that is to say gathering together channels of low indices, and the content of channels in a high-energy range, that is to say gathering together channels of higher indices. The range of low indices extends between the indices $n_{inf1}$ and $n_{inf2}$, while the range of high indices extends between $n_{sup1}$ and $n_{sup2}$, with $n_{sup2} > n_{inf2}$ and preferably $n_{inf2} \leq n_{sup1}$. For example, $n_{inf1}$, $n_{inf2}$, $n_{sup1}$ and $n_{sup2}$ are respectively equal to 1, 30, 50 and 130, we have:

$$x_4 = \frac{\sum_{n=ninf1}^{n=ninf2} Sp(En)}{\sum_{n=nsup1}^{n=nsup2} Sp(En)} = \frac{\sum_{n=1}^{n=30} Sp(En)}{\sum_{n=50}^{n=130} Sp(En)}$$

The fifth, sixth and seventh parameters are rates of change between two different channels, respectively situated in a low-index range $[m_{inf1}, m_{inF2}]$, in a medium-energy range $[m_{ave1}, m_{ave2}]$ and in a high-energy range $[m_{sup1}, m_{sup2}]$, with $m_{inf2} < m_{ave2} < m_{sup2}$ and preferably $m_{inf2} \leq m_{ave1}$ and/or $m_{ave2} \leq m_{sup1}$. For example, $m_{inf1}$, $m_{inf2}$, $m_{ave1}$, $m_{ave2}$, $m_{sup1}$, $n_{sup2}$ are respectively equal to 1, 40, 40, 80, 80, 120, so that $$x_5 = \frac{Sp(E_{n=minf2}) - Sp(E_{n=minf1})}{m_{inf2} - m_{inf1}} = \frac{Sp(E_{n=40}) - Sp(E_{n=1})}{39}$$

$$x_6 = \frac{Sp(E_{n=mave2}) - Sp(E_{n=mave1})}{m_{ave2} - m_{ave1}} = \frac{Sp(E_{n=80}) - Sp(E_{n=40})}{40}$$

$$x_7 = \frac{Sp(E_{n=msup2}) - Sp(E_{n=msup1})}{m_{sup2} - m_{sup1}} = \frac{Sp(E_{n=120}) - Sp(E_{n=80})}{40}$$

By rate of change, what is meant is a ratio between a difference of the contents of two channels over a difference of the index of these two channels.

The eighth parameter $x_8$ corresponds to an estimation of the effective atomic number $Z_{eff}$ of the material. Such an estimation may be established, with the help of the transmission spectrum Sp, according to a method described in patent application WO2015091083 mentioned previously as prior art, and in particular between pages 16 and 19 of this application. As indicated in connection with the description of the prior art, the effective atomic number corresponds to a combination, in particular on the basis of a weighted sum, of the atomic numbers of the various chemical elements constituting a material, the weighting terms being the mass fractions or atomic fractions of each chemical element. The scheme described in application WO2015091083 is aimed at establishing a likelihood function in the course of a calibration phase, and to estimate the value of the effective atomic number which maximizes this likelihood function.

According to a variant, use is made of a ninth parameter $x_9$ representing the thickness $EP_{ref}$ in a reference material, multiplied by the density of this reference material. Patent application FR 15 55438, filed on 15 Jun. 2015, describes how, with the help of a transmission spectrum Sp, it may be considered that the examined material is equivalent to two thicknesses ($EP_1$, $EP_2$), termed equivalent thicknesses, of two reference materials ($Ref_1$, $Ref_2$). This patent application describes the establishment of a likelihood function, during a calibration phase, based on known reference materials, and of various thicknesses. This likelihood function is thereafter implemented so as to determine the equivalent thicknesses in said reference materials, with the help of the transmission spectrum Sp of an examined sample, in particular according to a maximum likelihood criterion. One of these reference materials may be polyethylene PE, in which case the ninth parameter $x_9$ corresponds to the equivalent thickness of polyethylene $EP_{PE}$, determined by implementing a scheme such as described in this patent application, multiplied by the density of the polyethylene $\rho_{PE}$. Thus, $x_9 = EP_{PE} \times \rho_{PE}$. This ninth parameter is optional.

These 9 parameters define a point M, representative of the transmission spectrum Sp, in a space $\xi$ termed the input space. The base B of this input space $\xi$ is formed by basis vectors ($v_1 \ldots v_P$) respectively associated with each parameter, in such a way that the projection of the point M onto each of these basis vectors corresponds to the value of the parameter with which this basis vector is associated. Stated otherwise, the parameters ($x_1, \ldots, x_p$) represent the point M coordinates in the input space $\xi$. They also correspond to the coordinates of a vector $V_M$, associated with the point M, of dimension (P, 1) and comprising the coordinates ($x_1, \ldots, x_p$) of the point M. This vector $V_M$ is called the vector of parameters, since it gathers together parameters representative of the transmission spectrum Sp.

The fourth step 400 is a projection step, in the course of which the vector of parameters $V_M$ is projected according to at least one projection vector $w_i$, so as to allow a classification of this point in a class representing a given material. This also corresponds to a projection of the point M according to said projection vector.

More precisely, an objective of the method is to determine the nature of a material by classing it in a predetermined class of materials. This yields a number C of classes $C_j$, with $1 \leq j \leq C$, each class corresponding to a material, and the method makes it possible to identify the class to which the examined material belongs. A number W of projection vectors $w_1 \ldots w_i \ldots w_W$ has been determined previously, each projection vector being of dimension (P,1), so as to project the vector of parameters $V_M$ according to each of these projection vectors. These projection vectors are defined during a calibration phase of the scheme described hereinafter, in conjunction with steps 100' to 400' represented in FIG. 3. They define a basis of an output space $\xi'$. These projection vectors are stored in a memory 22 linked to the processor 20.

The projection according to each of the projection vectors amounts to determining the coordinates ($y_1, \ldots, y_W$) of the vector of parameters $V_M$ in the output space $\xi'$, these coordinates allowing a classification of the point in one of the C classes of materials. Each coordinate $y_w$, with $1 \leq w \leq W$, represents a classification parameter. By classification parameter is meant a parameter on the basis of which the classification is performed.

It is observed that the radiation transmitted 14 is firstly represented:
- by a transmission spectrum Sp, of dimension (N,1),
- then by a vector of parameters $V_{M,\xi}$ of dimensions (P,1), representing the coordinates $(x_1, \ldots, x_p)$ of a point M, representative of the spectrum Sp, in the input space $\xi$, with P≤N;
- then by a vector of parameters $V_{M,\xi'}$ of dimension (W, 1) representing the coordinates $(y_1, \ldots, y_w)$ of said point M in the output space $\xi'$, of dimension W, this space being associated with a basis B' defined by the W projection vectors $(w_1 \ldots w_i \ldots w_W)$. The coordinates $(y_1, \ldots, y_W)$ then constitute the classification parameters.

The number W of projection vectors is less than or equal to P. Preferably, the number W of projection vectors is equal to the number C of classes minus one, but it may also be lower. Hence, preferably, W=C-1, but it is also possible to have W≤C-1. In this example, it is considered that W=C-1.

The fifth step 500 is a classification step, making it possible to allot a class $C_j$ to the analyzed material, this class being representative of the nature of this material, or of a group of materials. It is determined as a function of the classification parameters $(y_1, \ldots, y_W)$, constituting the coordinates of the vector of parameters $V_{M,\xi'}$, in the output space $\xi'$.

This step is conventional, and amounts to identifying, in the output space $\xi'$, the class to which the vector of parameters $V_{M,\xi'}$ representing the spectrum Sp in this space belongs. The nature of the analyzed material is then considered to be that of the material associated with this class. The identification of the closest class can be carried out by calculating a distance between the vector of parameters and a vector representing the center of each class, this distance being able to be weighted by a dispersion term specific to each class. This type of operation is well known to the person skilled in the art.

In this example, the number of class C is equal to 6, each class $C_j$, 1≤j≤6 representing respectively TNT (the acronym standing for Trinitrotoluene), Polyethylene, PMMA (Polymethyl methacrylate), the PTFE (Polytetrafluoroethylene), water and Nylon.

The projection step 400 requires the use of at least one projection vector $w_i$, or of a set of projection vectors $(w_1 \ldots w_i \ldots w_W)$.

These projection vectors are defined during a training phase, carried out prior to the projection, and comprising steps 100' to 400', represented in FIG. 3 and described hereinbelow.

The first step 100' of the training phase is aimed at determining a plurality of calibration samples, whose nature is known and is representative of the materials that one wishes to identify subsequently. In this example, 24 calibration samples $Cal_j^k$ have been used, each calibration sample $Cal_j^k$ being of nature j, corresponding to a class $C_j$, and of thickness k, the latter being expressed in cm.

In this example, there are:
- four calibration samples $Cal_1^{k=2}$, $Cal_1^{k=4}$, $Cal_1^{k=8}$, $Cal_1^{k=12}$ of TNT, corresponding to class $C_1$;
- four calibration samples $Cal_2^{k=2}$, $Cal_2^{k=4}$, $Cal_2^{k=8}$, $Cal_2^{k=12}$ of Polyethylene, corresponding to class $C_2$;
- four calibration samples $Cal_3^{k=2}$, $Cal_3^{k=4}$, $Cal_3^{k=8}$, $Cal_3^{k=12}$ of PMMA, corresponding to class $C_3$;
- four calibration samples $Cal_4^{k=2}$, $Cal_4^{k=4}$, $Cal_4^{k=8}$, $Cal_4^{k=12}$ of PTFE, corresponding to class $C_4$;
- four calibration samples $Cal_5^{k=2}$, $Cal_5^{k=4}$, $Cal_5^{k=8}$, $Cal_5^{k=12}$ of water, corresponding to class $C_5$;
- four calibration samples $Cal_6^{k=2}$, $Cal_6^{k=4}$, $Cal_6^{k=8}$, $Cal_6^{k=12}$ of nylon, corresponding to class $C_6$.

The second step 200' of the training phase is a step of determining a plurality of calibration spectra, for example 20 calibration spectra $Sp(Cal_j^k,l)$, for each calibration sample $Cal_j^k$. Each calibration spectrum $Sp(Cal_j^k,l)$ corresponds to the realization l of a calibration spectrum relating to the calibration sample $Cal_j^k$ of nature j and of thickness k. l is an integer greater than or equal to 1. In this example, 1≤l≤20.

Figure 4:
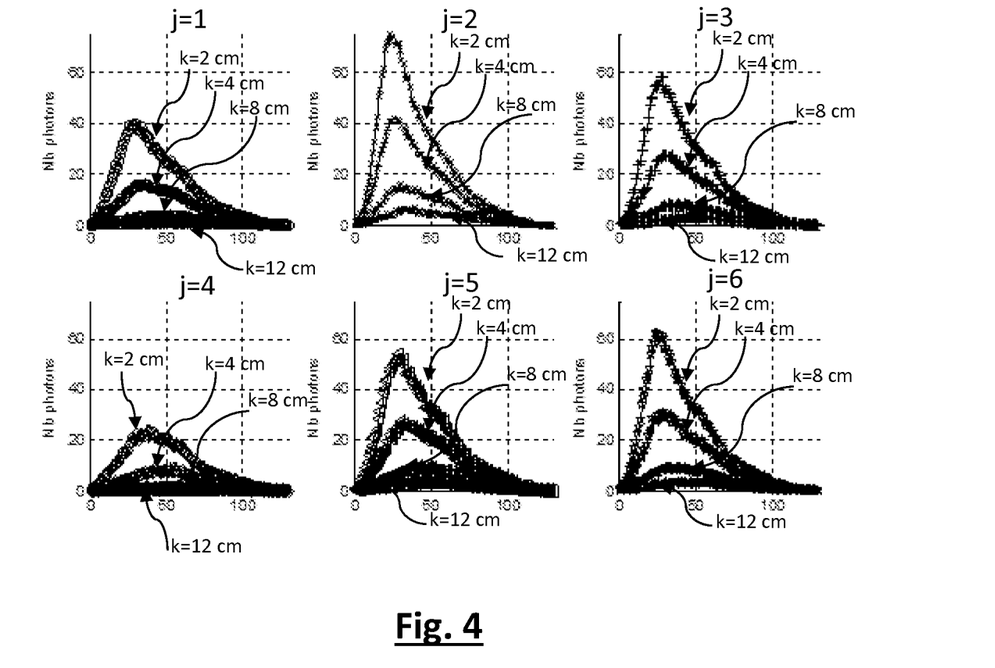
FIG. 4 represents the transmission spectra of various materials of nature j and of various thicknesses k. In each of these figures, the abscissa axis corresponds to the reference of each channel of the spectrum, while the ordinate axis "Nb Photons" represents the number of photons detected per channel.

These calibration spectra can be produced experimentally or simulated with the aid of a calculation code, for example on a statistical calculation code based on a scheme of Monte-Carlo type or other code known to the person skilled in the art. In the case of a simulation, each calibration spectrum is affected by noise that can be modeled by Poisson noise. FIG. 4 represents examples of calibration spectra, obtained for various calibration samples, of various thicknesses k, corresponding respectively to the classes j=1, j=2, j=3, j=4, j=5 and j=6.

In this example, each class is associated with a particular material. It is however possible that a class is associated with a mixture of materials, or with materials of one and the same group, for example materials considered to be inoffensive, or potentially dangerous, or else very dangerous.

The third step 300' of the training phase is a step of reducing the number of variables, or dimensionality reduction, in which P calibration parameters $(x_1^{j,k,l}, \ldots, x_p^{j,k,l})$ representative of each calibration spectrum $Sp(Cal_j^k,l)$ are determined with the help of this spectrum. It is understood that these parameters are identical to those described in conjunction with step 300. Thus, each calibration spectrum $Sp(Cal_j^k,l)$ can be represented, by a point $M(Cal_j^k,l)$, whose coordinates are $(x_1^{j,k,l}, \ldots, x_p^{j,k,l})$, these coordinates also constituting the terms of a calibration vector $V_M(Cal_j^k,l)$.

The fourth step 400' consists in determining W projection vectors $w_1, \ldots, w_W$, with W≤C-1, making it possible to obtain an optimal classification of each calibration spectrum $Sp(Cal_j^k,l)$. By optimal classification is meant that a maximum number of calibration spectra $Sp(Cal_j^k,l)$ are classed in the class $C_j$ corresponding to the nature j of the calibration sample.

These projection vectors can be obtained by a predictive discrimination analysis technique, known by the acronym LDA (Linear Discrimination Analysis), this scheme conferring a discriminating power which is particularly beneficial relative to other techniques for reducing dimensionality, for example decomposition into principal components (or PCA: Principal Component Analysis).

Figure 5:
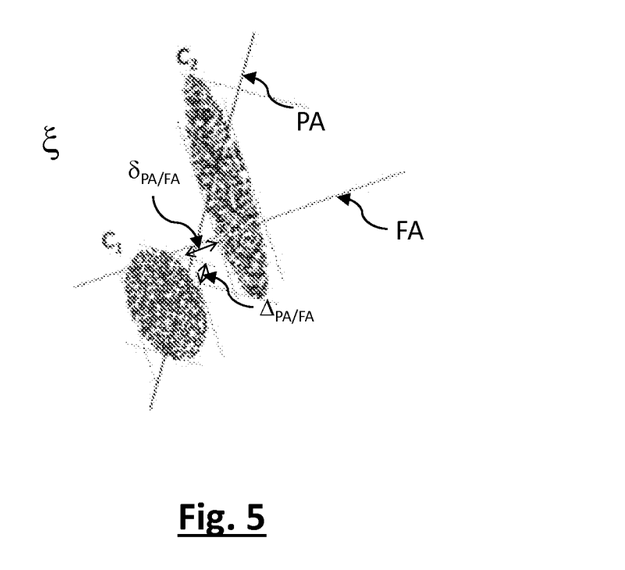
FIG. 5 represents two populations belonging to two different classes $C_1$ and $C_2$, as well as two axes FA and PA suitable for the classification of these populations according to one of these classes.

Applied to two classes, LDA classification amounts to determining an axis, termed the Fisher discriminating axis, allowing a separation between the populations belonging to two classes. FIG. 5 is an example representing two classes $C_1$ and $C_2$, represented in a two-dimensional input space $\xi$. Each class comprises a population represented by points, forming two ovoid sets. We have also represented the principal axis PA, determined by PCA, as well as the discriminating Fisher axis FA, determined by LDA. When the population of each class is projected onto the principal axis PA, an overlap range $\Delta_{PA/FA}$ is observed, in which certain points of the classes $C_1$ and $C_2$ lie above one another after projection. This projection does not therefore allow sharp separation between the two classes. Conversely, when the population of each class is projected onto the discriminating Fisher axis FA, the projected points of each class do not overlap and are a non-zero distance $\delta_{PA/FA}$ apart, attesting to correct separation between the two classes. In this example, the output space $\xi'$, of dimension 1, corresponds to the FA axis.

In a general manner, LDA classification is based on a discriminating criterion, determined by a comparison, generally taking the form of a ratio, between:
    a first term, representative of an inter-class dispersion,
    and a second term, representative of an intra-class dispersion.

This criterion may be a so-called Fisher discriminating criterion, such as defined hereinafter.

A discriminating criterion such as this makes it possible to define a projection vector, defining a discriminating axis, in such a way that the data projected according to this axis are used as classification parameters.

The inter-class or intra-class dispersions mentioned hereinabove are determined with the aid of the calibration vectors $V_M(Cal_j^k,l)$ associated with calibration materials $Cal_j^k$ of different classes j.

Let $m_j$ be the vector of dimension (P,1), representing the mean of the calibration vectors $V_M(Cal_j^k,l)$ associated with one and the same class $C_j$. The vector $m_j$ is such that for any integer p such that $1 \le p \le P$, $m_j(p)=\text{mean}_{k,l}[V_M(Cal_j^k,l)(p)]$. It is possible to define an inter-class dispersion matrix $\Sigma_{inter}$, of dimension C×C, such that:

$$\Sigma_{inter} = \frac{1}{c}\sum_{j=1}^{c}(m_j - m)(m_j - m)^T$$

m designating the mean vector of the mean vectors $m_j$ associated with each class j, in such a way that $m=\text{mean}_j[m_j]$, the operator mean designating the arithmetical mean, the exponent T designating the transpose operator.

We also define an intraclass dispersion matrix $\Sigma_{intra}$, of dimension (P,P) such that $$\Sigma_{intra} = \sum_{j=1}^{c} S_j$$

With, for each class j, $$S_j = \sum_{k,l}(V_M(Cal_j^K, L) - M_J)(v_m(Cal_j^k, l) - m_j)^T$$

The projection vectors sought, of dimension (P,1), are those which maximize the Fisher criterion J(w), mentioned above, such that $$J(w) = \frac{w^T \Sigma_{inter} w}{w^T \Sigma_{intra} w}$$

The solution vectors w correspond to the eigenvectors of a matrix $\Sigma$ of dimension (P,P) such that $$\Sigma = \Sigma_{intra}^{-1} \times \Sigma_{inter}$$

We then determine a set $w_1, \ldots, w_W$ of W projection vectors $w_i$, with $1 \le i \le W$, and $W \le C-1$. In this example, $W=C-1$, so that a set of projection vectors $w_1, \ldots, w_{c-1}$ is determined.

The projection vector $w_1$ can be the eigenvector associated with the eigenvalue whose absolute value is the highest, the vectors $w_i$ of lower indices being associated respectively with the eigenvalues whose absolute value is less and less high. Stated otherwise, each projection vector $w_i$ is such that the eigenvalue associated therewith exhibits an absolute value greater than that associated with the projection vector $w_{i+1}$, with $1 \le i \le W-1$.

The projection vectors defined during step 400' are stored in the memory 22, so as to be used during the projection step 400 during the determination of an unknown material.

This step of determining the projection vectors $w_1, \ldots, w_W$ requires the inversion of the matrix $\Sigma_{intra}$. The dimensionality reduction step 300' is important when the number N of channels of the calibration spectra is greater than 10 or 20, this generally being the case. Indeed, if the matrix $\Sigma_{intra}$ was determined directly with the help of the calibration spectra $(Cal_j^k,l)$, of dimension (N, 1), it would probably not be invertible, owing to the overly high value of N. Step 300' then makes it possible to use a reduced number of P parameters. The dimensionality reduction therefore allows the definition of the projection vectors $w_i$.

Figure 6:
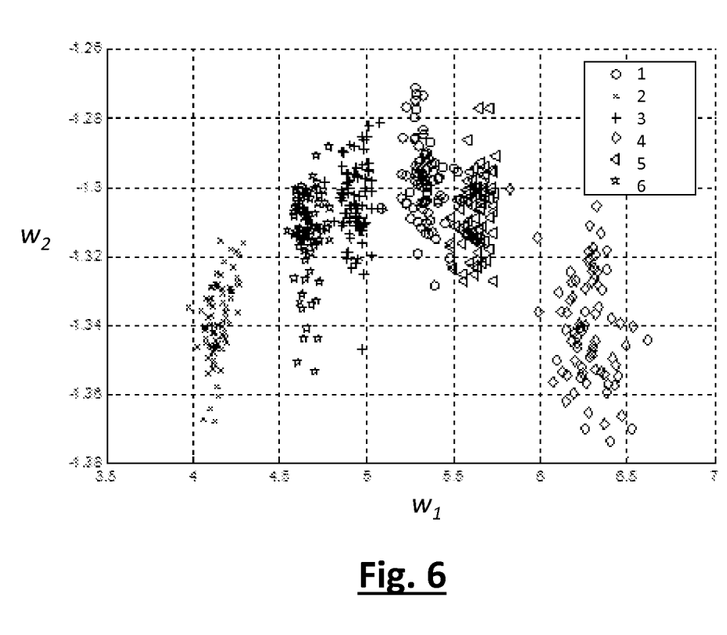
FIG. 6 represents points, each point representing a calibration spectrum associated with calibration material, in a plane defined by two projection vectors $w_1$ and $w_2$.

In order to test the relevance of the projection vectors determined subsequent to step 400', a first trial has been carried out by projecting the calibration spectra $Sp(Cal_j^k,l)$ established during step 200'. In the course of this first trial, steps 200 to 400 described previously are performed based on these calibration spectra. FIG. 6 represents each point $M(Cal_j^k,l)$, representative of a calibration spectrum, in a plane defined by the first two projection vectors $w_1$ and $w_2$. It is observed firstly that each point $M(Cal_j^k,l)$ of one and the same material class j is grouped together with the other points of the same class, corresponding to a different thickness k and/or realization l. Thus, each class $C_j$ appears well grouped.

Let $y_{1,j}^k$ be the coordinate of the point $M(Cal_j^k,l)$ along the axis $w_1$, that is to say the projection of $M(Cal_j^k,l)$ along this axis. It is observed that the coordinates $y_{1,j}^k$ allow correct separation of each class, the points associated with the classes j=1, j=2, j=3, j=4, j=5 and j=6 being projected respectively into the value ranges: [5.1-5.5]; [4-4.4]; [4.8-5.1]; [6-6.5]; [5.5-5.8]; [4.5-4.8].

Thus, according to this example, a single projection, according to a single projection vector, in this instance $w_1$, can make it possible to perform correct classification.

A noteworthy result is that the classification is robust in relation to the thickness k of the material.

Figure 7:
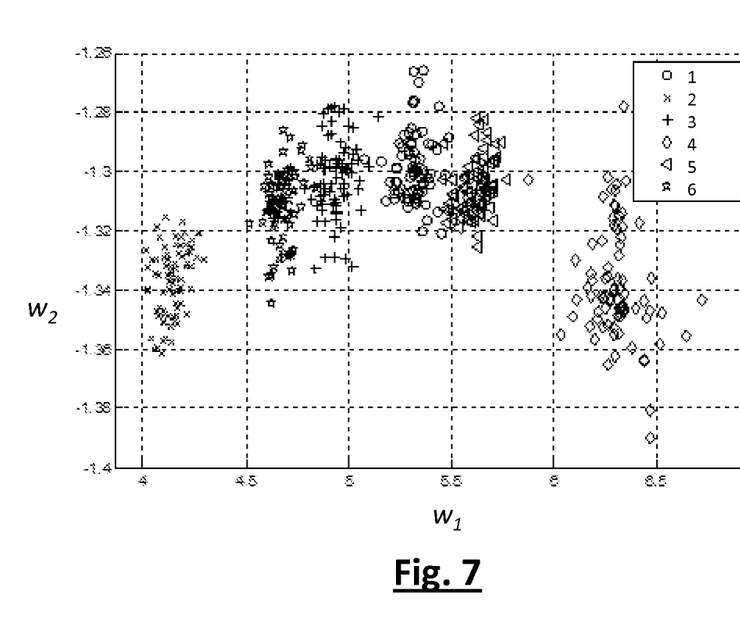
FIG. 7 represents points, each point representing a test spectrum associated with a test material, in a plane defined by two projection vectors $w_1$ and $w_2$.

A second trial has been carried out, by simulating test spectra $Sp(Test_j^k)$, each spectrum corresponding to a material of nature j and of thickness k. These test spectra are simulated. It is considered that each simulation corresponds to a realization of step 200 of acquiring a spectrum.

For each test spectrum $Sp(Test_j^k)$, steps 300 and 400 described previously are implemented, step 400 making it possible to obtain the coordinates $(y_1, \ldots, y_{c-1})$ representing each spectrum according to the projection vectors $w_1, \ldots, w_{c-1}$ obtained with the aid of the calibration spectra.

FIG. 7 represents each point $M(Test_j^k)$, representative of each spectrum $Sp(Test_j^k)$, in a plane defined by the projection vectors $w_1, w_2$. It is observed again that each spectrum is correctly classed. It is noted that the projection according to the first projection vector $w_1$, making it possible to determine a classification parameter $y_{1,j}^k$, allows more reliable classification than a projection according to the second projection vector $w_2$, giving rise to a classification parameter $y_{2,j}^k$.

Figure 8:
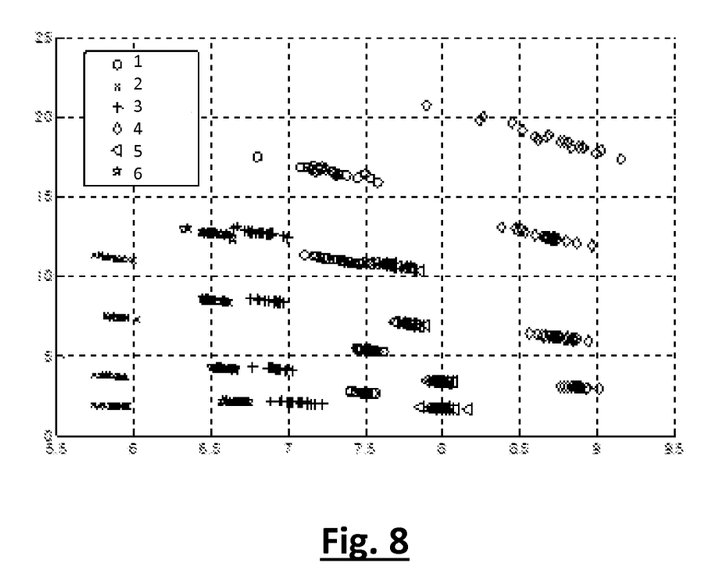
FIG. 8 represents points corresponding to test spectra, in a plane defined by two axes. The abscissa axis represents an estimation of the effective atomic number and the ordinate axis represents an estimation of an equivalent length of polyethylene, multiplied by the density of the polyethylene.

The test spectra Sp(Test$_j^k$) have moreover been processed with the aid of the schemes, mentioned previously, described respectively in patent applications WO2015091083 and FR1555438 mentioned above. Thus, an estimation of the effective atomic number $Z_{eff}$ and an estimation of the equivalent thickness $L_{PE}$ in a reference material of Polyethylene type have been obtained.

FIG. 8 represents points representative of each of these spectra in a plane whose abscissa axis represents the estimation of the effective atomic number Zeff and whose ordinate axis represents the equivalent thickness $L_{PE}$ of Polyethylene multiplied by the density of the Polyethylene.

It is observed that the classification on the basis of the estimation of the effective atomic number allows correct estimation of the nature j of the material, while the classification according to the equivalent thickness $L_{PE}$ of Polyethylene allows segmentation of the materials according to their thickness k.

We have compared the performance of the classification carried out, on the basis of the test spectra Sp(Test$_j^k$), respectively according to the estimation of the effective atomic number $Z_{eff}$ and according to a classification method according to the invention, by implementing 5 projection vectors $w_1, \ldots, w_5$.

The performance of each classification is estimated by calculating an indicator $DP_{j,j'}$ representing the discriminating power of a scheme for discriminating two different classes j and j'.

The discriminating power of each classification parameter Z is defined by the expression:

$$DP\,(Z)_{j,j'} = \frac{(\text{mean}(z_j) - \text{mean}(z_{j'}))}{\sigma_{zj}^2 - \sigma_{zj'}^2},$$

with:

mean $(Z_j)$ and mean $(Z_{j'})$: means of the classification parameters Z obtained by implementing materials of class j and j' respectively;

$\sigma_{zj}^2$ and $\sigma_{zj'}^2$: variances of the classification parameters Z obtained by implementing materials of class j and j' respectively.

The higher this discriminating power DP $(Z)_{j,j'}$, the better the classification parameter Z makes it possible to discriminate two classes j and j'.

Table 1 represents the discriminating power DP $(Z)_{j,j'}$ with Z=$Z_{eff}$, the classification parameter then being the estimation of the effective atomic number Zeff.

Table 2 represents the discriminating power DP $(Z)_{j,j'}$ with $$Z = \sum_{i=1}^{5} y_i,$$

each term $y_i$ being determined by the projection of a vector of parameters of a test spectrum $V_M(\text{Test}_j^k)$ according to a projection vector $w_i$ such as described above.

TABLE 1

| | \multicolumn{6}{c}{j'} | | | | | |
| j | 1 | 2 | 3 | 4 | 5 | 6 |
|---|---|---|---|---|---|---|
| 1 | X | 87.7 | 6.5 | 30.8 | 5.0 | 22.7 |
| 2 | X | 0 | 65.7 | 204.5 | 155.9 | 44.1 |
| 3 | X | 0 | 0 | 67.7 | 26.1 | 5.9 |
| 4 | X | 0 | 0 | 0 | 13.3 | 107.9 |
| 5 | X | 0 | 0 | 0 | 0 | 57.9 |
| 6 | X | 0 | 0 | 0 | 0 | 0 |

TABLE 2

| | \multicolumn{6}{c}{j'} | | | | | |
| j | 1 | 2 | 3 | 4 | 5 | 6 |
|---|---|---|---|---|---|---|
| 1 | X | 144.0 | 14.4 | 49.3 | 8.8 | 45.4 |
| 2 | X | X | 79.5 | 251.4 | 251.2 | 42.7 |
| 3 | X | X | X | 100.3 | 50.2 | 9.1 |
| 4 | X | X | X | X | 26.7 | 149.7 |
| 5 | X | X | X | X | X | 110.0 |
| 6 | X | X | X | X | X | X |

The discriminating powers shown in table 2 are on average 1.6 times higher than those shown in table 1.

Thus, the invention makes it possible to carry out more reliable classification.

The invention will be able to be implemented in the field of non-destructive testing of materials, in particular the checking of baggage.

The invention claimed is:

1. A method for classifying a material comprising:
   i) irradiating a sample comprising the material using an electromagnetic ionizing radiation as incident radiation, produced by an irradiation source;
   ii) detecting a radiation transmitted by the sample by a spectrometric detector, the sample being disposed between the irradiation source and the spectrometric detector, and acquiring a transmission spectrum of the radiation thus detected, the transmission spectrum being representative of an energy distribution of the radiation transmitted, the transmission spectrum comprising a number of channels, and representing a quantity of photons detected per channel, each channel corresponding to an energy range;
   iii) determining a set of parameters from the transmission spectrum, the set of parameters forming the coordinates of a vector of parameters, the vector of parameters representing the transmission spectrum, in an input space, the number of parameters of the set of parameters being strictly less than the number of channels of the transmission spectrum;
   iv) projecting the vector f parameters according to at least one projection vector, to obtain at least one projected datum, each projected datum resulting from the projection of the vector of parameters according to a projection vector;
   v) classifying the material using each projected datum.

2. The method of claim 1, wherein there is a predetermined number of classes of materials, and the classifying v) classifies the materials according to one of the classes of material.

3. The method of claim 2, wherein the projecting iv) comprises projecting the vector of parameters into an output space, the projection vectors forming an output basis of the output space.

4. The method of claim 3, wherein the number of vectors forming the output basis is strictly less than the number of classes of materials.

5. The method of claim 1, wherein the transmission spectrum is normalized, term by term, by a spectrum of the incident radiation, the spectrum being representative of the energy distribution of the incident radiation.

6. The method of claim 1, wherein the number of parameters is less than the number of channels of the transmission spectrum, divided by 2.

7. The method of claim 1, wherein the transmission spectrum is defined on a plurality of channels, and wherein at least one parameter comprises:
   a reference of the channel of the transmission spectrum comprising the maximum number of detected photons;
   or a ratio between the contents of two different channels;
   or a rate of change between the contents of two different channels.

8. The method of claim 1, wherein each projection vector is determined during a training phase, carried out using calibration materials whose nature is known, the calibration materials defining at least two distinct classes of materials, the training phase comprising:
   obtaining calibration spectra, each calibration spectrum being representative of an energy distribution of a radiation transmitted by a calibration material when the calibration material is disposed between the irradiation source and the spectrometric detector;
   determining a set of calibration parameters, using each calibration spectrum, the calibration parameters forming the coordinates of a calibration vector, to obtain a plurality of calibration vectors corresponding to each class.

9. The method of claim 8, wherein at least one projection vector is determined by calculating, and by maximizing, using each calibration vector, a discriminating criterion, determined by a comparison between:
   a first term representative of an inter-class dispersion;
   a second term, representative of an intra-class dispersion.

10. The method of claim 8, wherein at least one projection vector is obtained by determining, using each calibration vector,
    a first matrix representative of an inter-class dispersion,
    a second matrix, representative of an intra-class dispersion,
    a third matrix, formed by a matrix product of a matrix inverse to the second matrix by the first matrix,
    the projection vector being an eigenvector of the third matrix.

11. The method of claim 8, wherein each projection vector is determined by linear discrimination analysis, by considering each calibration vector.

12. A device for characterizing a material contained in a sample comprising:
    an irradiation source, configured to emit an ionizing electromagnetic radiation, as incident radiation, toward the sample,
    a spectrometric detector configured to detect a radiation transmitted by the sample when the sample, exposed to the incident radiation, is interposed between the irradiation source and the spectrometric detector,
    wherein the device comprises a processor, configured to receive data measured by the spectrometric detector and to implement iii) and iv) of the method of claim 1, the processor being connected to a memory in which at least one projection vector is stored.

13. An non-transitory computer readable information recording medium, comprising instructions for execution of iii) and iv) of the method of claim 1, the instructions being executed by a processor.

* * * * *